United States Patent [19]

Beppu et al.

[11] Patent Number: 4,761,374

[45] Date of Patent: Aug. 2, 1988

[54] THERMALLY STABLE TRYPTOPHANASE, PROCESS FOR PRODUCING THE SAME, AND THERMALLY STABLE TRYPTOPHANASE-PRODUCING MICROORGANISM

[75] Inventors: Teruhiko Beppu, 5-2, Horinouchi 1-chome, Sugunomi-ku, Tokyo; Seibun Suzuki, Tokyo, both of Japan

[73] Assignee: Teruhiko Beppu, Tokyo, Japan

[21] Appl. No.: 871,315

[22] Filed: Jun. 6, 1986

[30] Foreign Application Priority Data

Jun. 8, 1985 [JP] Japan ................................ 60-124546

[51] Int. Cl.$^4$ .......................... C12N 9/88; C12N 1/20; C12P 39/00; C12R 1/07; C12R 1/01
[52] U.S. Cl. ...................................... 435/232; 435/42; 435/253; 435/822; 435/832
[58] Field of Search .......................... 435/232, 42, 253

[56] References Cited

U.S. PATENT DOCUMENTS 3,808,101  4/1974  Enei et al. ........................ 435/232 X Primary Examiner—Lionel M. Shapiro
Attorney, Agent, or Firm—Sherman and Shalloway

[57] ABSTRACT

A thermally stable tryptophanase having (1) an optimum temperature for activity at a pH of 8.0 of about 70° C., and (2) such thermal stability that it is not thermally deactivated when maintained at temperatures up to about 65° C. and a pH of 8.0 for 40 minutes. The thermally stable tryptophanase can be produced by cultivating in a tryptophan-containing culture medium a thermally stable tryptophanase-producing bacterium which does not grow alone in said medium but grows there in the presence of Bacillus sp. strain S, and obtaining the resulting thermally stable tryptophanase from the culture broth. The thermally stable tryptophanase-producing microorganism for use in the above process is a novel organism.

9 Claims, 3 Drawing Sheets

THERMALLY STABLE TRYPTOPHANASE, PROCESS FOR PRODUCING THE SAME, AND THERMALLY STABLE TRYPTOPHANASE-PRODUCING MICROORGANISM

This invention relates to heat-resistant tryptophanase which is useful, for example, in the industrial synthesis of tryptophan and is not described in the prior literature, a process for producing the tryptophanase by a fermentation technique, and to a thermally stable tryptophanase-producing microorganism for use in the above process which microorganism is not described in the prior literature.

More specifically, this invention relates to a thermally stable tryptophanase which is clearly distinguished in thermal stability characteristics from known tryptophanases, and particularly to a thermally stable tryptophanase having (1) an optimum temperature for activity at a pH of 8.0 of about 70° C., and (2) such thermal stability that it is not thermally inactivated when maintained at temperatures up to about 65° C. and a pH of 8.0 for 40 minutes.

This invention also relates to a process for producing the novel thermally stable tryptophanase by a fermentation technique, and a novel thermally stable tryptophanase-producing microorganism suitable for use in the practice of this process. In particular, it pertains to a novel thermally stable tryptophanase-producing bacterium, and to a process for producing a thermally stable tryptophanase which comprises cultivating the bacterium, and recovering the resulting thermally stable tryptophanase from the culture broth.

Tryptophanase is known as an enzyme which catalyzes not only an alpha, beta splitting reaction forming pyruvate, indole and ammonia from L-tryptophan in the presence of pyridoxalphosphate (PLP) but also a reaction synthesizing L-tryptophan from indole, pyruvate and ammonia which is a reaction reverse to the above reaction. Tryptophanases have been isolated from microorganisms, mainly from a group of Enterobacteriaceae such as *Escherichia coli, Aeromanas liquefaciens* and *Proteus rettgeri.*

These known tryptophanases have an optimum temperature for activity at a pH of 8.0 of about 33 to 35° C. and are substantially inactivated thermally when maintained at temperatures of at least about 40° C. at a pH of 8.0 for 40 minutes. Hence, in use, these tryptophanases are much restricted in heat-resistant characteristics involving the reaction temperature and thermal stability.

The present inventors have worked in order to create a tryptophanase which overcomes the aforesaid technical difficulty. Consequently, they succeeded in isolating a tryptophanase-producing bacterium which is novel and not described in any known literature and has unique growth characteristics from a soil sample. Experiments of the present inventors show that this tryptophanase does not grow alone in a natural medium or a tryptophan-containing synthetic medium, but grows there in the presence of a Bacillus sp. strain S. It has been found that this novel bacterium produces a thermally stable tryptophanase which has an optimum temperature for activity at a pH of 8.0 of about 70° C. and shows such thermal stability that it is not inactivated thermally when maintained at temperatures up to about 65° C. and a pH of 8.0 for 40 minutes, and in this regard, quite differs from the known tryptophanases.

Investigations of the present inventors have shown that the new bacterium capable of producing the novel thermally stable tryptophanase of this invention does not grow alone in any culture media for microorganisms, but actively grows and proliferates only when the Bacillus strain S is present and grows simultaneously, for example, in a synthetic liquid medium containing tryptophane and pH-adjusted with phosphates, at a temperature of about 58 to about 63° C. with weak agitation or by standing to give a mixed cultivation product having strong enzymatic activity.

It has further been found by the investigations of the present inventors that the Bacillus sp. strain S is a new strain which belongs to the genus Bacillus forming spores and can be purely cultivated in general media for bacteria; and that it shows physiological properties represented by (i)' negative indole formation and (ii)' negative nitrate reduction and does not show the ability to produce tryptophanase either alone or in the presence of the thermally stable tryptophanase-producing bacterium in a tryptophan-containing synthetic medium.

It is an object of this invention therefore to provide a novel thermally stable tryptophanase and a process for its production.

Another object of this invention is to provide the aforesaid thermally stable tryptophanase-producing bacterium.

The above and other objects of this invention along with its advantages will become apparent from the following description and the accompanying drawings.

BRIEF DESCRIPTION OF THE DRAWINGS

FIGS. 4—1 to 4—5 are graphs plotting the residual tryptophanase activity at temperatures of 50° C., 55° C., 60° C., 65° C. and 70° C., respectively, as a function of incubation time.

Figure 1:
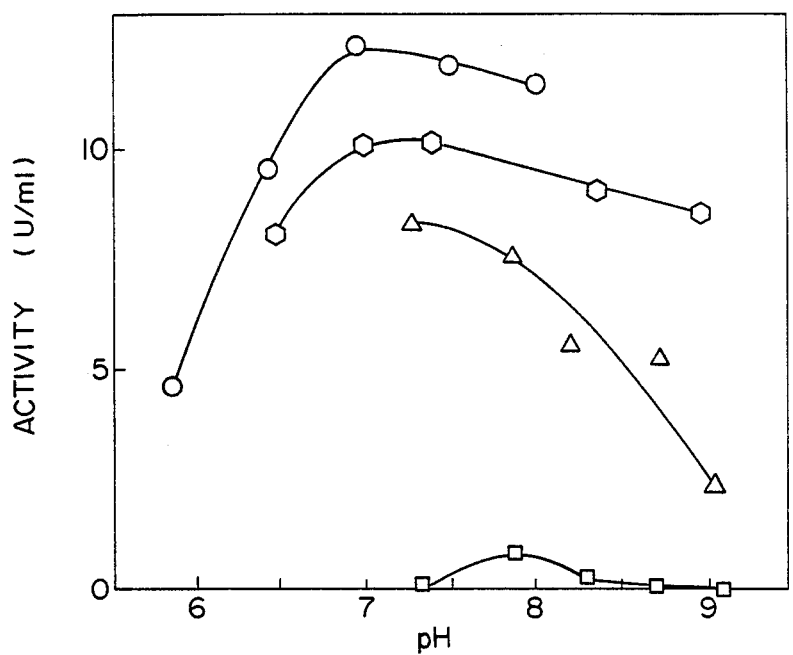
FIG. 1 is a graph plotting tryptophanase activity of the enzyme as a function of pH.

The new thermally stable tryptophanase-producing bacterium of this invention which does not grow alone in a tryptophan-containing synthetic medium but grows there in the presence of Bacillus sp. strain S to produce and accumulate the thermally stable tryptophanase within the cells is isolated from a soil sample derived from a high-temperature environment such as hot springs and composts.

The method of isolation is described below.

A soil sample derived from a high-temperature environment such as hot springs and composts is put in a Trp-PEP liquid medium to be described which is a tryptophanase inducing medium whose pH is adjusted with a phosphate. It is subjected to shaking culture at about 60° to 70° C. in an L-type test tube, and the cultivation giving indole formation detected by the Kovac's reagent is used to separate the tryptophanase-producing strain. The tryptophanase-producing strain growing at about 60° C. is purified from the culture by a dilution method and further by utilizing resistance to Bacitracin to give a purified tryptophanase-producing strain.

The culture containing the tryptophanase-producing strain is subjected to agar solid culture in a customary manner and colony separation is attempted. However, no colony formation is observed in all kinds of agar solid media tested. The cell suspension recovered from the culture is plated on a Trp-PEP agar medium whose surface is covered with a membrane filter (100 to 200 cells per plate), and cultivated at about 60° C. to form colonies. With regard to the formed colonies, indole formation is detected by the Kovac's reagent, and the colonies can be divided into indole-producing colonies and indole-non-producing colonies.

The indole-producing colonies are obtained as mixed colonies of two kinds of bacilli of different cell sizes, and the indole-non-producing colonies can be obtained as colonies composed of one of the two types of bacilli.

A strain which grows either alone or as a mixture in the above tryptophan-containing synthetic medium but does not show the ability to produce tryptophanase by itself (indole-non-producing strain) has been named Bacillus sp. strain S by the present inventors. A thermally stable trypotophanase-producing bacterium which can be isolated as a mixture with Bacillus sp. strain S, and does not grow alone in a tryptophan-containing synthetic medium but grows there in the presence of the Bacillus sp. strain S to produce and accumulate a thermally stable trypotphanase within the cells has been named Bacterium strain T by the present inventors.

The thermally stable tryptophanase-producing bacterium of this invention which can be isolated as a mixture with the Bacillus sp. strain S from a soil sample derived from a high-temperature environment as stated above can be continuously cultivated and preserved as the aforesaid mixture in a synthetic liquid medium (Trp-PEP liquid medium) of the following composition containing tryptophan at the pH adjusted with a phosphate, or can be stored as L-dry cells (mixture).

Trp-PEP liquid medium:

| Composition | Per 100 ml |
|---|---|
| L-tryptophan | 0.2 g |
| Polypeptone | 0.5 g |
| Yeast extract | 0.1 g |
| $K_2HPO_4$ | 0.3 g |
| $KH_2PO_4$ | 0.1 g |
| $MgSO_4.7H_2O$ | 0.05 g |
| Pyridoxal-5'-phosphate | 0.05 g |

The pH of the medium is 6.8 to 7.0

The thermally stable tryptophanase-producing bacterium, Bacterium strain T, which can be isolated as a mixture with Bacilus sp. strain S from a soil sample derived from a high-temperature environment as above and can be cultivated and preserved as such or can be stored as L-dry cells can be separated from the co-growing Bacillus sp. strain S, for example by the following methods.

(a) Bacterium stain T and Bacillus sp. strain S can be separated from each other by a technique of fractional centrifugation based on the utilization of the differences in cell size.

(b) Bacterium strain T and Bacillus sp. strain S are different in sensitivity to lysozyme, and Bacillus sp. strain S is more sensitive to it. By utilizing this difference, the Bacillus sp. strain S can be lysed selectively. As a result, Bacterium strain T can be separated from the mixture.

As far as the tests attempted by the present inventors, the thermally stable tryptophanase-producing bacterium of this invention does not grow alone in any of natural and synthetic media for microorganisms. Hence, except its morphological characteristics and physiological characteristics with regard to catalase, its microbiological characteristics cannot be determined.

Bacterim strain T (a) Morphological characteristics
(1) Size and shape of cells: Rod-shaped (diameter 0.25–0.35 µm, length 1.5–7 µm), usually present single.
(2) Pleomorphism of cells: none
(3) Mobility: none
(4) Spores: none
(5) Gram stain: negative, invariable (b) Cultural characteristics on various media
(1) Nutrient agar plate culture: no growth
(2) Nutrient agar slant culture: no growth
(3) Nutrient liquid culture: no growth
(4) Nutrient gelatin stab culture: no growth
(5) Litmus milk: no growth
(6) Tryptophan-containing synthetic medium (Trp-PEP liquid medium): No growth when cultivated alone. But it grows in the presence of Bacillus sp. strain S (FERM BP-809).

In the present invention, the expression that the "microorganism does not grow alone in a tryptophan-containing synthetic medium but grows there in the presence of Bacillus sp. strain S to produce and accumulate a thermally stable tryprophanase within the cells" means that it does not grow alone in the aforesaid Trp-PEP medium but grows there in the presence of Bacillus sp. strain S to produce and accumulate the thermally stable tryptophanase within the cells.

(c) Physiological characteristics (+: positive; −: negative)
(1) Reduction of nitrate: test impossible in the pure culture. But (+) in the presence of Bacillus sp. strain S.
(2) Denitrification: test impossible
(3) MR test: test impossible
(4) VP test: test impossible
(5) Indole production: test impossible in the pure culture. But (+) in the presence of Bacillus sp. strain S.
(6) Formation of hydrogen sulfide: test impossible
(7) Hydrolysis of starch: test impossible
(8) Utilization of citric acid: test impossible
(9) Utilization of inorganic nitrogen sources: test impossible
(10) Formation of pigments: test impossible
(11) Urease: test impossible
(12) Oxidase: test impossible
(13) Catalase: (+)
(14) Growth range (pH, temperature, etc.): test impossible
(15) Aerobiosis: test impossible
(16) O-F test: test impossible
(17) Formation of acids and gases from sugars: test impossible (d) Other characteristics
(1) DNA has a guanine cytocine (GC) content, determined by Tm method, of about 65 mole %.
(2) It grows in the tryptophan-containing synthetic medium shown in (b), (6) above in the presence of Bacillus sp. strain S at a temperature of about 58° to 63° C. with weak agitation or by standing.

The bacterium having the above characteristics is not at all described in any known literature including Bergey's Manual of Determinative Bacteriology, 8th edition, and has been named Bacterium strain T by the present inventor. The above bacterium isolated for the first time by the present inventors is deposited as a mixture with Bacillus sp. strain S in Fermentation Research Institute, Agency of Industrial Science and Technology, Japan under deposit number FERM BP-810 in accordance with Budapest Treaty on the international recognition of the deposit of microorganisms for the purposes of patent procedure.

Bacillus sp. strain S in the presence of which the thermally stable tryptophanase-producing bacterium of this invention can grow in a tryptophan-containing synthetic medium is a novel strain of the genus Bacillus forming spores, and can be purely cultivated in general media for bacteria. Its microbiological characteristics are described below.

Bacillus sp. stain S (a) Morphological characteristics
(1) Size and shape of cells: Rod-shaped (diameter 0.6–0.9 $\mu$m, length 2.5–6.0 $\mu$m), usually present single.
(2) Pleomorphism of cells: none
(3) Mobility: +, peripheral flagella
(4) Spores: Elliptical, 1.1×2.0 $\mu$m. Formed within, and at one end of, the cells
(5) Gram stain: positive
(b) Cultural characteristics on various media
1. Nutrient agar medium—Smooth, colorless or semi-transparent, glistening
2. Nutrient liquid medium—Surface growth forming white membrane.
(c) Physiological characteristics (+: positive; —: negative)
(1) Reduction of nitrate: +
(2) MR test: +
(3) VP test: —
(4) Indole production: —
(5) Resistance to 0.02% $NaN_3$: +
(6) Catalase: +
(7) Growth in the presence of 5% salt: —
(8) Growth range: Growth at a pH of 5.7 (+); growth temperature 66° C. (upper limit), 40° C. (lower limit).
(9) Aerobiosis: anaerobic
(10) Fermentation of starch: +
(11) Fermentation of arabinose and xylose: —
(12) Fermentation of mannitol: —
(13) Fermentation of glucose: +, gas formation (—).

Since it grows at 65° C., it is similar to *Bacillus stearothermophilus*. But test results with regard to (9) anaerobic growth, (5) resistance to 0.02% $NaN_3$ and (8) growth at pH 5.7 do not agree with each other, and there is no corresponding strain in Begey's Manual of Determinative Bacteriology, 8th edition. Accordingly, it has been identified as a new strain and named Bacillus sp. strain S by the present inventors. This strain isolated for the first time by the present inventors is deposited in Fermentation Research Institute, Agency of Industrial Science and Technology, Japan under deposit number FERM BP-809 in accordance with Budapest Treaty on the international recognition of the deposit of microorganisms for the purposes of patent procedure.

Thus, according to this invention, there is provided a process for producing a thermally stable tryptophane, which comprises cultivating the microorganism described in detail hereinabove, i.e. the thermally stable tryptophanase-producing bacterium which does not grow alone in a tryptophan-containing synthetic medium but grows there in the pesence of Bacillus sp. strain S, and recovering the thermally stable tryptophanase from the culture broth.

The cultivation may be carried out by inoculating the thermally stable tryptophanase producing bacterium in a culture medium containing suitable carbon sources, nitrogen sources and minerals in the presence of Bacillus sp. strain S. Examples of the carbon sources are glucose, starch, maltose, sodium succinate and sodium acetate. Examples of the nitrogen sources are organic or inorganic nitrogen sources such as $NH_2Cl$, $(NH_4)_2SO_4$, Casamino acid, peptone and yeast extract. Examples of the minerals are $K_2HOP_4$, $KH_2PO_4$, $MgSO_4\cdot7H_2O$, $FeCl_3$ and vitamins.

The cultivation can be carried out aerobically in a liquid medium containing L-tryptophan in addition to the aforesaid carbon sources, nitrogen sources, mineral and vitamins. The method of cultivation can be properly chosen, and may, for example, be stationary culture, shaking culture and aeration-agitation culture. The cultivation is carried out at a pH of about 6 to about 8 and a temperature of about 55° to about 65° C. for about 1 to 3 days.

After the cultivation, the cells are collected by centrifugal separation, filtration, etc. For example, the desired thermally stable tryptophanase can be extracted by disrupting the cells by, for example, alumina grinding, and obtaining the thermally stable tryptophanase-containing fraction from the resulting cell extract by, for example, ammonium sulfate fractionation. The enzyme may be purified by a suitable purifying technique such as ion exchange, gel filtration and column chromatography.

The thermally stable tryptophanase of the invention which can be produced as above is a novel enzyme which can be clearly distinguished from the conventional tryptophanases in that it has an optimum temperature for activity at a pH of 8.0 of about 70° C. and such thermal stability characteristics that it is not thermally inactivated when maintained at temperatures up to about 65° C. at a pH of 8.0 for 40 minutes.

The properties of the thermally stable tryptophanase of this invention are shown below.

1. Activity
It forms pyruvic acid, indole and ammonia from L-tryptophan in the presence of pyridoxalphosphate.

2. Substrate specificity
It decomposes L-tyrptophane, S-methyl-L-cysteine, L-cysteine and 5-methyl-L-tryptophan.

3. Optimal PH and stable pH
Optimum pH=7.0–7.5 (65° C. ) (see FIG. 1)
Stable pH=6–10 (25° C., 2 days [see FIG. 2])

FIG. 1 of the accompanying drawings shows the tryptophanase activity of the enzyme of this invention which was measured at various pH values (at 65° C. ) using (1) 50mM potassium phosphate buffer (—o—o—), (2) 50mM glycine-NaOH buffer containing 10mM KCl (—□—□—), (3) 50mM glycine/NaOH buffer containing 5mM $(NH_4)_2SO_4$ (—◇—◇—) and (4) 50mM glycine-NaOH buffer (—△—△—). From the reuslts of (1), (2) and (3), the optimum pH is determined to be 7.0-7.5 (65° C.).

Figure 2:
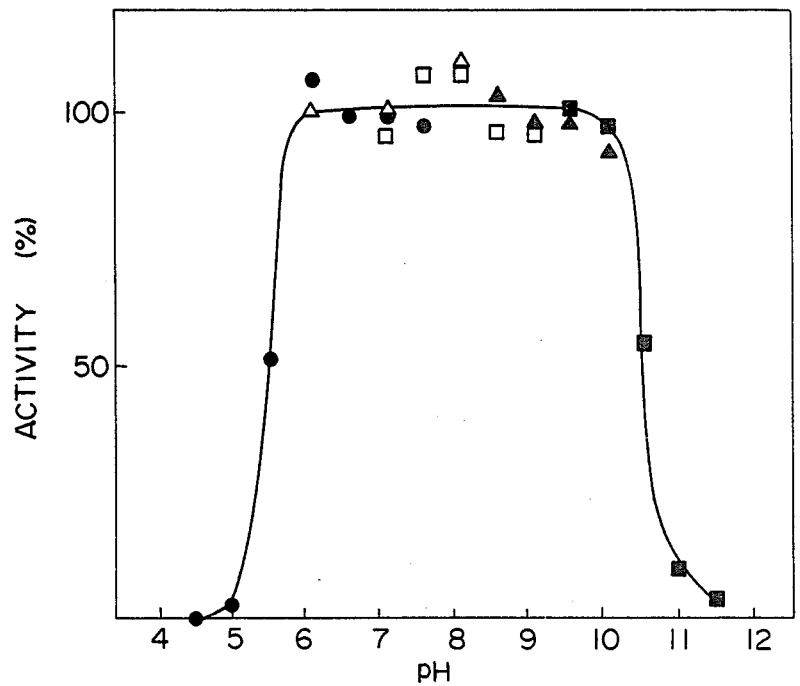
FIG. 2 is a graph plotting the residual tryptophanase activity after treatment at 25° C. for 2 days as a function of pH.

FIG. 2 of the accompanying drawings shows the results of measurement of residual tryptophanase activity of the enzyme of this invention after it has been treated at 25° C. for 2 days at various pH values (at 25°) using various 50mM buffers containing 10mM KCl and 10 μM pyridoxal-5'-phosphate (citrate-Na₂HPO₄ buffer —●—●—; K₂HPO₄-KH₂PO₄ buffer —Δ—Δ—; Tris-HCl buffer —□—□—; glycine-NaOH buffer —▲—▲—; NaHCO₃-NaOH buffer —■—■—). From the results shown in FIG. 2, the stable pH of the enzyme of this invention is determined to be 6-10 (25° C., 2 days).

4. Method of measuring activity

Measured in accordance with the method of Yamada et al. as follows. In 4.0ml of a reaction mixture containing 10 micromoles of L-tryptophan, 0.4 micromole of pyridoxalphosphate (PLP)), 200 micromoles of K₂HPO₄-KH₂PO₄ (pH 8.0), the enzyme is incubated at 65° C. for 10 minutes. Then, 1.0 ml of a 30% aqueous solution of trichloroacetic acid (TCA) is added to stop the reaction. Indole formed in the reaction system is quantitatively determined by the method of E. McEvoy-Bowe [The ANALYST, vol. 88, pages 893-894 (1963)]. The activity is expressed in units in which 1 U is the amount in micromoles of indole formed during 1 minute.

5. Optimum temperature

The optimum temperature for tryptophan decomposing activity is about 70° C. (pH=8.0) (see FIG. 3).

Figure 3:
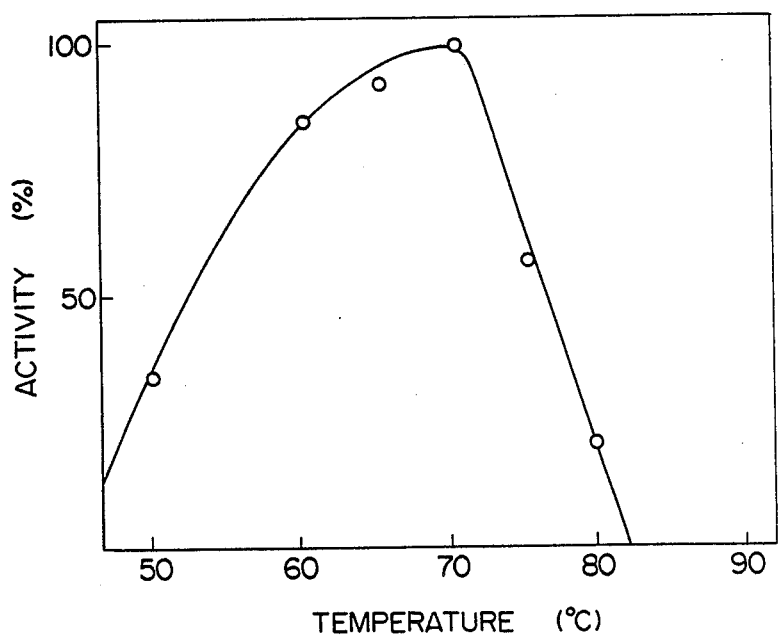
FIG. 3 is a graph plotting tryptophanase activity of the enzyme as a function of temperature.

FIG. 3 of the accompanying drawings show the tryptophanase activity of the enzyme determined at various temperatures for 10 minutes in 50mM K₂HPO₄₅-KH₂PO₄ buffer (pH 8.0). From the results, the optimum temperature for activity at pH 8.0 is determined to be about 70° C.

6. Inactivation conditions by temperature.

Figures 1, 4:
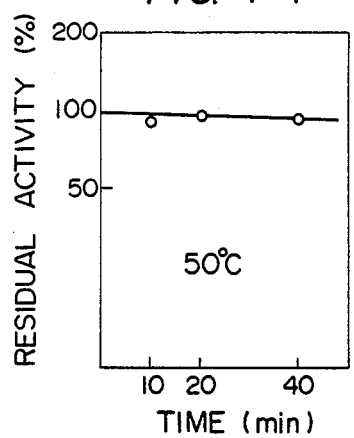
Figures 2, 4:
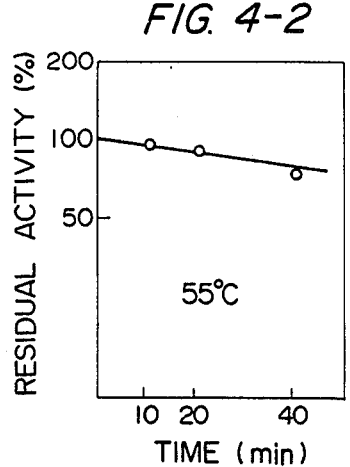
Figures 3, 4:
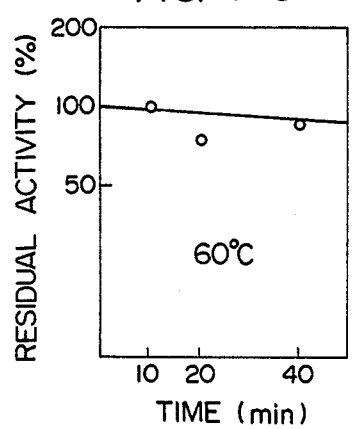
Figure 4:
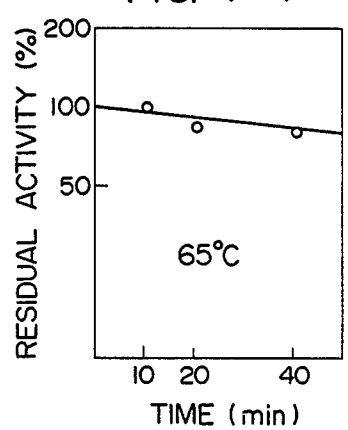
Figures 4, 5:
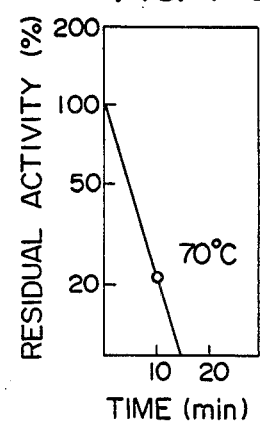

FIG. 4 of the accompanying drawing depicts the relation between the residual tryptophanase activity and the incubation time (minutes) at temperatures of 50° C. (FIG. 4-1), 55° C. (FIG. 4-2), 60° C. (FIG. 4-3), 65° C. (FIG. 4—4), and 70° C. (FIG. 4—5) in order to show the thermal inactivation characteristics of the thermally stable tryptophanase of this invention.

It is not inactivated at temperatures up to about 65° C. (pH=8.0, incubation time, 40 minutes) (see FIGS. 4-1 to 4-4)

At about 70° C. (pH=8.0, incubation time 10 minutes), the enzyme shows a residual activity of about 20% (see FIG. 4-5).

7. Inhibition, activation and stabilization

Activation of the enzyme with K+ and NH₄+ is observed. For example, when these ions are added to a glycine-NaOH buffer, the enzyme is activated in the buffer (see FIG. 1).

8. Method of purification

The cells obtained by cultivation in a tryptophanase inducing culture medium are disrupted by alumina grinding, and fractionated with a 50% saturated ammonium sulfate solution using 50mM K₂HPO₄-KH₂PO₄ buffer (pH 8.0) containing 10 μM PLP and 1mM mercapotoethanol. The precipitate is suspended, dialyzed, and purified by using DEAE-Toyoparl, gel filtration with Ultrogel AcA34, and hydroxylapatite HT.

9. Molecular weight

Its molecular weight is determined to be about 44,000 to about 46,000 by SDS gel electrophoresis.

Since the thermally stable tryptophanase of this invention has excellent thermal stability characteristics unlike the conventional tryptophanases, it can overcome the technical difficulties of the conventional tryptophanases in regard to reaction temperatures or thermal stability, and can be advantageously utilized industrially.

The following Examples illustrate the present invention more specifically.

EXAMPLE 1

Isolation of Bacterium T strain as a thermally stable tryptophanase-producing bacterium:

(1) One gram of a compost sample was added to 10 ml of a Trp-PEP liquid medium, and cultivated under shaking for 1 day at about 60° C. in an L-type test tube. Indole production was confirmed by the Kovac's reagent, and then, a portion (0.1 ml) of the culture was inoculated into 10 ml of a fresh Trp-PEP liquid medium, and repeatedly cultivated to form a culture having well grown indole-forming cells. The culture (0.1 ml) was inoculated into 10 ml of a Trp-PEP liquid medium containing 1 mg/liter of Bacitracin, and cultivated in the same way as above.

The resulting culture broth was diluted to about 100,000 times with a sterilized physiological saline, and 0.1 ml of the dilution was plated on a Trp-PEP agar medium (containing 1.5% of agar) whose surface is covered with a membrane filter (Toyo TM-2). Thus, colonies in which Bacterium strain T (to be sometimes abbreviated as strain T) and Bacillus sp. strain S (to be sometimes abbreviated as strain S) grew in a mixed state and colonies composed of strain S alone were separately collected.

(2) One milliliter of the mixed colonies of strain T and strain S obtained in (1) described above was inoculated into 200 ml of a tryptophan-containing synthetic medium (Trp-PEP liquid medium), and cultivated at 60° C. for about 30 hours. About 4 hours later, active growth of strain S took place and subsequently, almost simultaneously with the stopping of growth of strain S, growth of strain T began. At the same time, strain S died rapidly. Finally, a culture in which at least 99% of the cells were strain T cells could be obtained. To decrease the proportion of the strain S cells further and to obtain a pure culture substantially composed of strain T cells alone, the strain T cells could be separated at any stage of the cultivation using a method based on the difference between strain T and strain S in resistance to a cell wall decomposing enzyme (lysozyme), or a centrifugal fractionation method as described below.

(1) Method using lysozyme:

Strain T and strain S were cultivated in a mixed state for 18 hours. Action of lysozyme under the following conditions resulted in selective lysis of strain S cells. Strain S cells present at that time in a proportion of about 25% of the total cell number decreased to less than one-thousandth of the entire cells by this treatment. Thus, a pure culture of strain T could be obtained.

Conditions:

The cells were incubated in a reaction mixture consisting of 300 micrograms/ml of egg white lysozyme, 200 micrograms/ml of EDTA, and 30 mg/ml of sodium citrate in 100mM sodium phosphate buffer (pH 7.0) at 35° C. for 15 minutes.

(2) Centrifugal fractionation method

A culture obtained by cultivating strain T and strain S in the mixed state for 20 hours was centrifuged at 1,000×G for 15 minutes to precipitate strain S cells selectively. Then, centrifugation was carried out at 14,000×G for 20 minutes to precipitate and separate strain T cells alone.

EXAMPLE 2

This example illustrates that strain T cannot be cultivated alone.

(1) Strain T cells separated from the mixed culture of strain T and strain S by the method shown in Example 1, (2) was inoculated in any of the following liquid media at 60° C. But in any of these media, no growth of strain T was observed.
1. Trp-PEP liquid medium
2. Ordinary nutrient medium
3. Heart infusion nutrient medium
4. Bovine serum + heart infusion nutrient medium
5. Yeast extract + heart infusion nutrient medium
6. Above media 1 to 5 + 0.5% agar (2) To demonstrate the possibility of cell products or cell components of strain S supporting the growth of strain T, strain S alone was inoculated in the Trp-PEP liquid medium and cultviated at 60° C. for about 12 hours. A supernatant of the culture and a cell-free extract obtained by ultrasonication were aseptically filtered, and added to the Trp-PEP liquid medium. Purely separated strain T cells were inoculated into the medium, but no proliferation of strain T was observed. Separately, cultivation of strain T was carried out in the presence of strain S cells whose cell division was stopped by streptomycin. But no growth of strain T was observed.

EXAMPLE 3

Enzyme production:

One and half liters of a tryptophan-containing synthetic medium (Trp-PEP liquid medium) in a 5-liter Erlenmeyer flask was inoculated with 5 ml of a mixed culture of strain T and strain S, and cultivated at 60° C. for 30 hours in a stationary condition. The culture broth was treated as in Example 1 to obtain 120 g of wet cells of strain T from 77.6 liters of the culture broth. The cells were disrupted by grinding with alumina, and then 166 ml of 50mM $K_2HPO_4$-$KH_2PO_4$ buffer (pH 6.5) containing 10 μM pyrioxal-5'-phosphate (PLP), 1mM 2-mercaptoethanol, and 250 μM phenylmethylsulfonyl fluoride (serine protease inhibitor) was added to give a crude enzyme solution. The enzyme was precipitated with 0–50% saturated ammonium sulfated fractions. The resulting crude enzyme preparation was treated with streptomycin to remove nucleic acid, and dialyzed, and adsorbed onto a column (2.6 cm in diameter × 12 cm) of DEAE-Toyopal (Toyo Soda Industry Co., Ltd.). The column was eluted by concentration gradient of 0→400 mM KCl (400 ml). Active fractions were collected and purified by gel filtration on a column (2.1 cm in diameter × 85 cm) of Ultrogel AcA34 (LKB Company). The purified fractions were further adsorbed onto a column (2.6 cm × 8 cm) of hydroxylapatite gel HT (Biorad Company). The column was eluted by concentration gradient of 0→300mM $(NH_4)_2SO_4$ (300 ml), and about 100 mg of tryptophanase was obtained from the active fractions.

The resulting enzyme had an optimum temperature for activity at a pH of 8.0 of about 70° C., and was not thermally inactivated when maintained at temperatures of up to about 65° C. and a pH of 8.0 for 40 minutes. The specific activity of this enzyme in tryptophan decomposition was at least 8 times as high as that of a commercial enzyme (37° C. ), and the activity of synthesizing tryptophan from indole, pyruvic acid and ammonia by a reverse reaction was also detected.

What is claimed is:

1. A thermally stable tryptophanase having
   (1) an optimum temperature for activity at a pH of 8.0 of about 70° C., and
   (2) such thermal stability that it retains at least about 80% residual activity when maintained at a temperature of 60° C. and a pH of 8.0 for 40 minutes.
2. The thermally stable tryptophanase of claim 1 which further has
   (3) activity such that it forms pyruvic acid, indole and ammonia from L-tryptophan in the presence of pyridoxal phosphoric acid,
   (4) such substrate specificity that it decomposes tryptophan, S-methyl-L-cysteine, L-cysteine and 5-methyl-L-tryptophan, and
   (5) an optimum pH range of 7.0 to 7.5 at 65° C. and a stable pH range of 6 to 10 at 25° C.
3. A process for producing a thermally stable tryptophanase, which comprises cultivating in a tryptophan-containing culture medium a thermally stable tryptophanase-producing bacterium, Bacterium strain T (FERM BP-810) and obtaining the resulting thermally stable trypophanase from the culture broth.
4. The process of claim 3 wherein the cultivation is carried out at a temperature of about 55° to about 65° C. and a pH of about 6 to about 8.
5. A thermally stable tryptophanase-producing bacterium which is Bacterium strain T (FERM BP-810).
6. The tryptophanase-producing bacterium of claim 5 which under cultivation conditions in the presence of Bacillus sp. strain S (FERM BP-809), shows positive indole production and positive nitrate reduction.
7. The thermally stable tryptophanase-producing bacterium of claim 5 wherein its DNA has a GC content, determined by the Tm method, of about 65 mole %.
8. The thermally stable tryptophanase-producing bacterium of claim 5 which is in the form of a mixture with Bacillus sp. strain S.
9. A mixture of the thermally stable trypotophanase-producing bacterium of claim 5 with Bacillus sp. strain S FERM BP-809.

* * * * *

UNITED STATES PATENT AND TRADEMARK OFFICE
CERTIFICATE OF CORRECTION

PATENT NO. : 4,761,374
DATED : August 2, 1988
INVENTOR(S) : TERUHIKO BEPPU, ET AL.

It is certified that error appears in the above-identified patent and that said Letters Patent is hereby corrected as shown below:

IN THE CLAIMS

Column 10, claim 3, line 36, delete "trypophanase", insert --tryptophanase--.

Signed and Sealed this

Twenty-ninth Day of November, 1988

Attest:

DONALD J. QUIGG

Attesting Officer

Commissioner of Patents and Trademarks